United States Patent
Ng et al.

(10) Patent No.: US 9,496,187 B2
(45) Date of Patent: Nov. 15, 2016

(54) SETUP FOR MULTIPLE CROSS-SECTION SAMPLE PREPARATION

(71) Applicant: GLOBALFOUNDRIES Singapore Pte. Ltd., Singapore (SG)

(72) Inventors: Tsu Hau Ng, Singapore (SG); Zhihong Mai, Singapore (SG); Mohammed Khalid Bin Dawood, Singapore (SG); Pik Kee Tan, Singapore (SG); Yamin Huang, Singapore (SG); Jeffrey Chor-Keung Lam, Singapore (SG)

(73) Assignee: GLOBALFOUNDRIES Singapore Pte. Ltd., Singapore (SG)

( * ) Notice: Subject to any disclaimer, the term of this patent is extended or adjusted under 35 U.S.C. 154(b) by 162 days.

(21) Appl. No.: 14/084,636

(22) Filed: Nov. 20, 2013

(65) Prior Publication Data
US 2015/0140688 A1    May 21, 2015

(51) Int. Cl.
*B24B 41/06* (2012.01)
*H01L 21/66* (2006.01)
*B24B 49/12* (2006.01)
*G01N 1/32* (2006.01)

(52) U.S. Cl.
CPC .............. *H01L 22/12* (2013.01); *B24B 49/12* (2013.01); *G01N 1/32* (2013.01); *H01J 2237/20* (2013.01)

(58) Field of Classification Search
CPC ........ B24B 49/12; B24B 49/10; B24B 41/06
USPC ............... 451/41, 28, 365, 37, 440, 364
See application file for complete search history.

(56) References Cited

U.S. PATENT DOCUMENTS

| | | | | |
|---|---|---|---|---|
| 5,272,844 A | * | 12/1993 | Burgess | B24B 37/30 269/58 |
| 5,800,254 A | * | 9/1998 | Motley | B24B 7/22 451/285 |
| 5,816,899 A | * | 10/1998 | Hart | B24B 41/06 269/71 |
| 8,506,355 B1 | * | 8/2013 | Patterson | B24B 49/04 451/285 |
| 2006/0099886 A1 | * | 5/2006 | Rubin | B24B 7/00 451/6 |

* cited by examiner

*Primary Examiner* — Robert Rose
(74) *Attorney, Agent, or Firm* — Horizon IP Pte. Ltd.

(57) ABSTRACT

A multiple-sample-holder polishing setup for cross-section sample preparation and a method of making a device using the same are presented. The multiple-sample-holder polishing setup includes a frame. The frame has a hollow center, one or more long and short rods and a recess for accommodating a polishing head. The setup includes one or more sample holders. The sample holder is to be attached to the one or more long and short rods of the frame. A paddle is affixed to each sample holder. A sample is attached to the paddle. The sample is coated with a thin epoxy layer prior to polishing thereby allowing for easy inspection for site of interests as well as quick material removal.

20 Claims, 9 Drawing Sheets

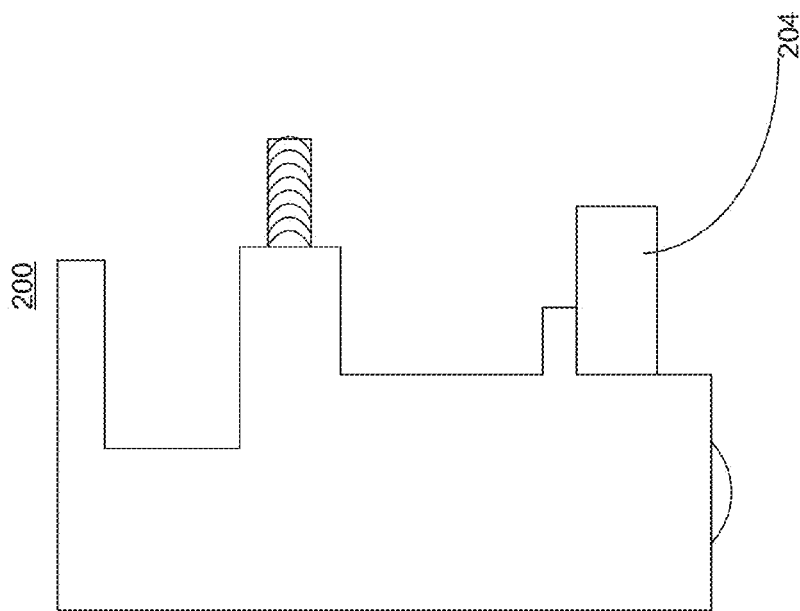
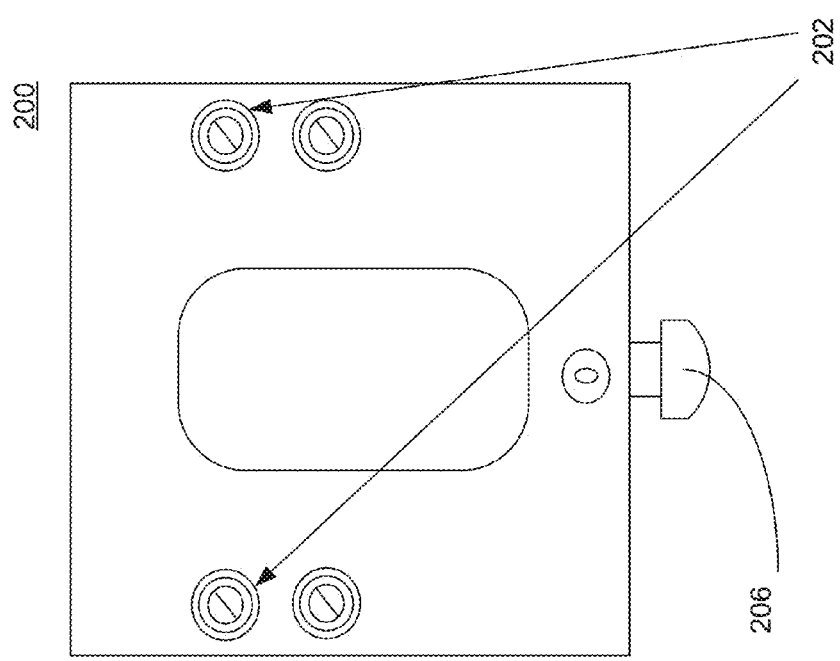

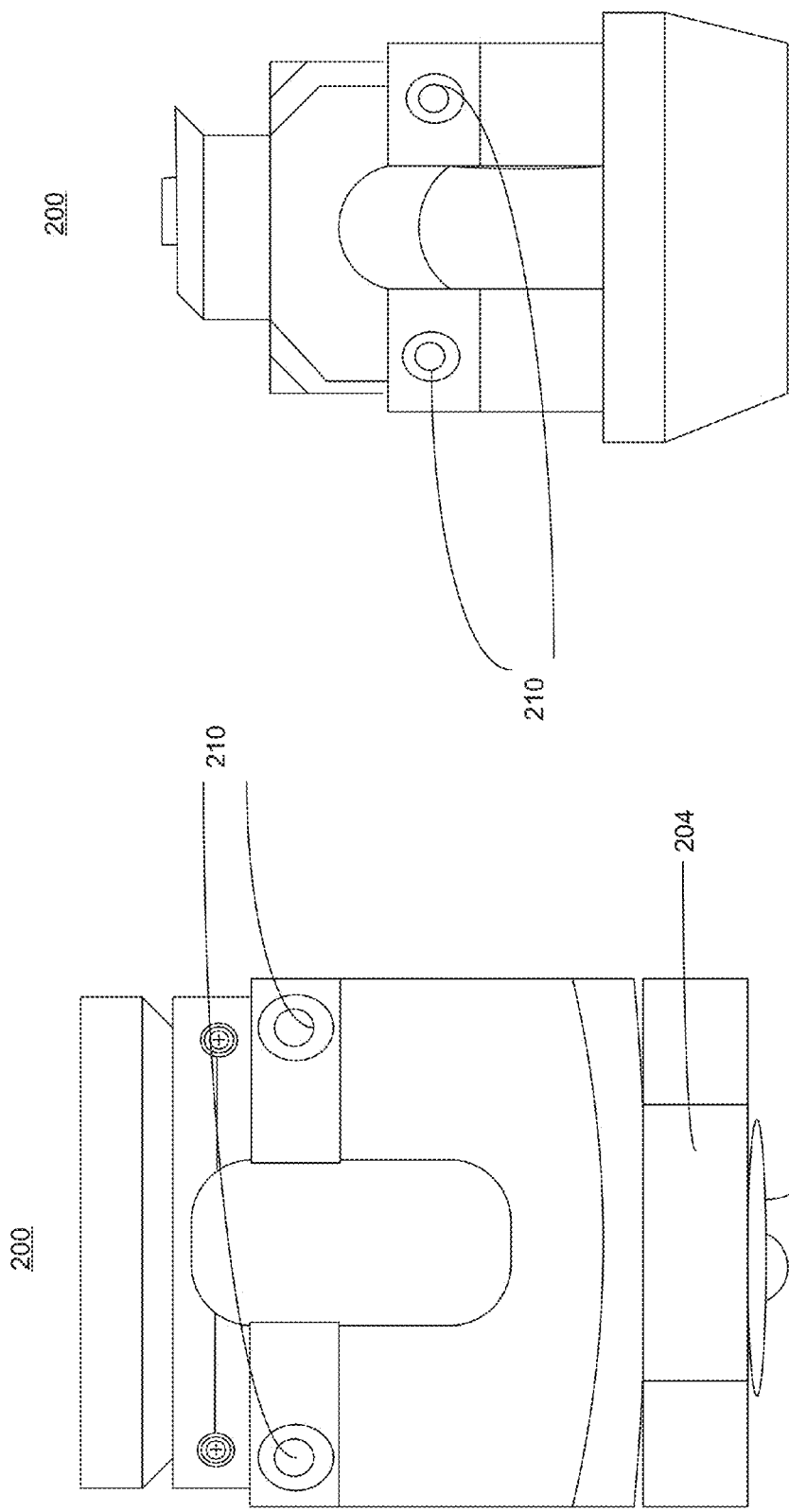

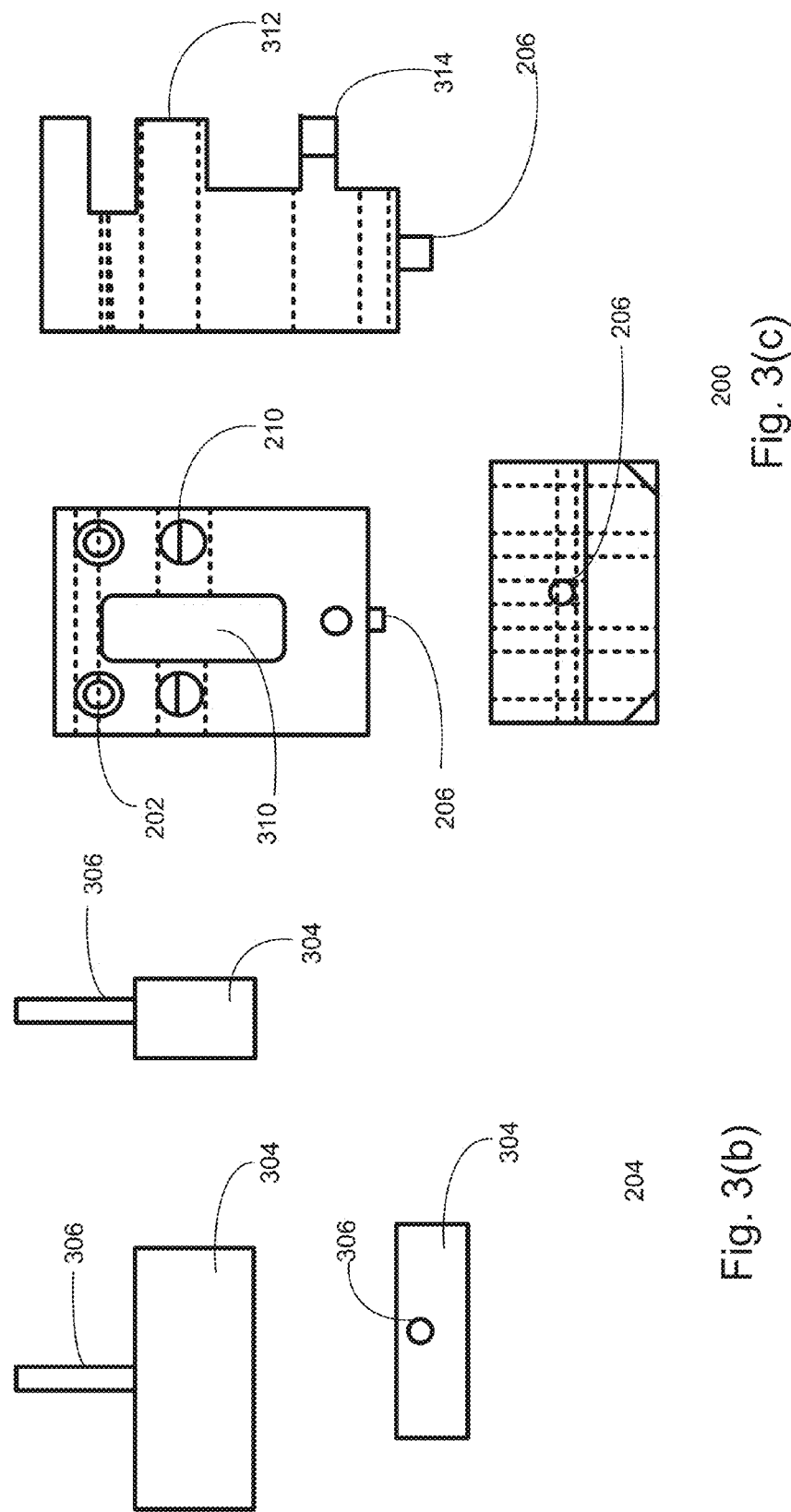

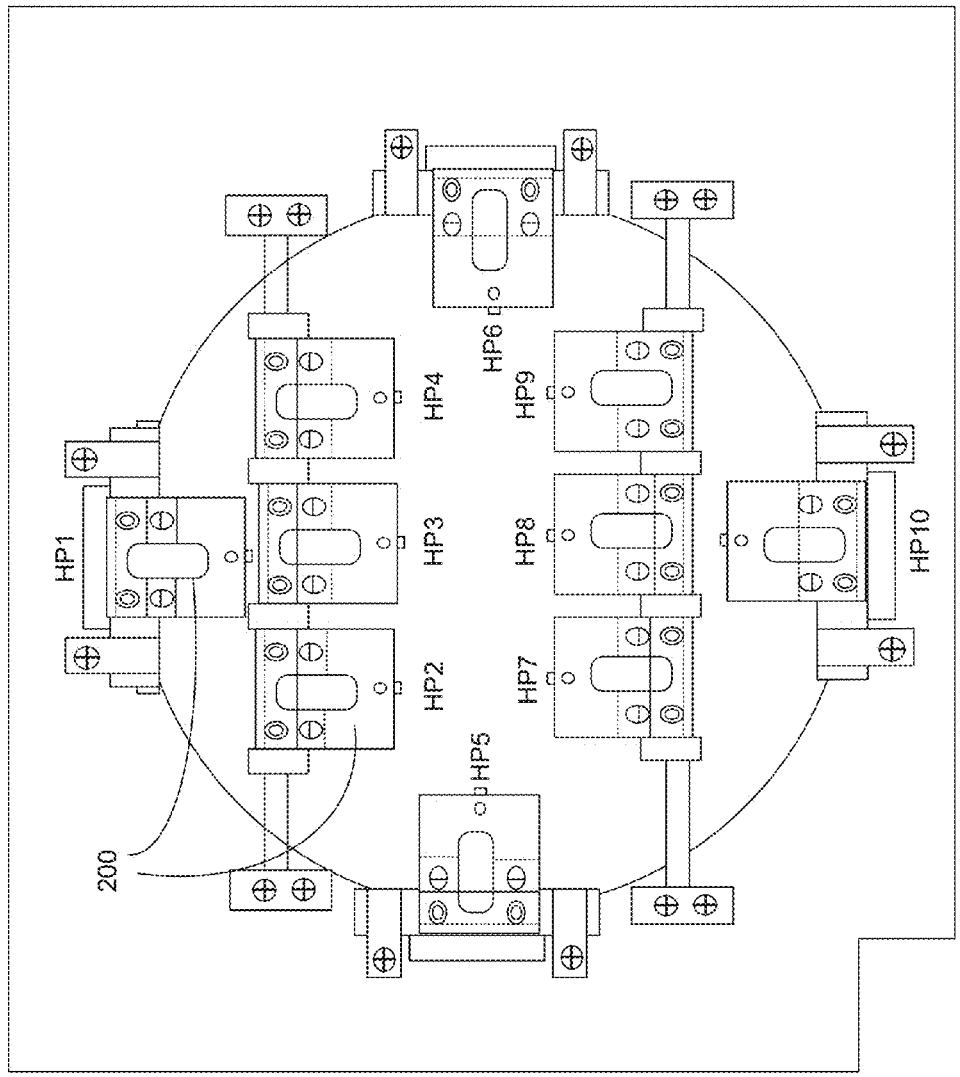

SETUP FOR MULTIPLE CROSS-SECTION SAMPLE PREPARATION

BACKGROUND

Sample preparation is a necessary step to facilitate the investigation of failure mechanism in an integrated circuit (IC) chip. The standard procedure involves the extraction of a die from the wafer, coating the die with a layer of protective epoxy and then mechanically polishing the cross-section of the die to the location of interest for inspection using the optical microscope, Scanning Electron Microscope (SEM), Atomic Force Microscopy (AFM) or Transmission Electron Microscope (TEM).

In conventional sample preparation, typically one sample is prepared at a time. While there are some commercial tools that are equipped with multi-sample polishing capability, these systems usually only polish the die in a planar direction. For tools which are able to perform cross-section polishing, these tools require the samples to be molded into a cylindrical form before they could be placed under the polishing head and the molding of epoxy into a cylindrical form requires a longer curing time. These tools are not equipped with level-adjustment capability while performing cross-section polishing.

In the process of the aforementioned molding, it is common to witness the formation of bubbles as the epoxy volume is typically large and air could be trapped as a result. The presence of bubble is undesirable as voids and non-uniformity could be created within the dried epoxy. Moreover, the presence of these voids could affect the ability of the epoxy to hold the internal structure of the sample during mechanical polishing. Besides affecting the support rigidity, the larger volume of epoxy will also take a longer time to be polished away, thus affecting throughput.

Furthermore, in embedding the sample within a thick (diameter of about 1 inch) epoxy cylinder, either the cross-section of the sample is visible but the planar surface would blocked by the thick epoxy or the planar surface is visible but the cross-section is blocked by the thick epoxy. Such poor sample visibility would affect the user's ability to determine if the site of interest has arrived.

From the foregoing discussion, it is desirable to provide a simple, economical and fast setup for multiple-sample cross-section polishing.

SUMMARY

Embodiments generally relates to a multiple-sample-holder polishing setup for cross-section sample preparation and the use of such setup for forming semiconductor devices.

In one embodiment, a multiple-sample-holder polishing setup is disclosed. The multiple-sample-holder polishing setup includes a frame. The frame has a hollow center, one or more long and short rods and a recess for accommodating a polishing head. The setup includes one or more sample holders. The sample holder is to be attached to the one or more long and short rods of the frame. A paddle is affixed to each sample holder and a sample is attached to the paddle. The sample is coated with a thin epoxy layer prior to polishing thereby allowing for easy inspection for site of interests as well as quick material removal.

In another embodiment, a method for preparing cross-section samples is presented. The method includes providing a frame having a hollow center and one or more long and short rods with one or more sample holder attached thereto. The method includes affixing a paddle to each of the one or more sample holders and the paddle having a sample attached thereto. The sample is polished. The sample is coated with a thin epoxy layer prior to polishing thereby allowing for easy inspection for site of interests as well as quick material removal.

In yet another embodiment, a method for forming a device is disclosed. The method includes forming an active device on a semiconductor substrate. The active device is formed by device fabrication parameters which are adjusted according to data received from inspection of one or more polished samples. The polished samples are prepared by providing one or more samples and providing a multiple-sample-holder polishing setup. The setup includes a frame having more than one sample holders affixed thereto. A paddle is affixed to each of the sample holders and the paddle has the sample attached thereto. The method includes polishing the sample. The sample is coated with a thin epoxy layer prior to polishing thereby allowing for easy inspection for site of interests as well as quick material removal. Data received is collated and analyzed from inspection of the site of interest. Device fabrication parameters are adjusted according to the collated and analyzed data and the aforementioned steps are repeated until the desired yield is achieved.

These advantages and features of the embodiments herein disclosed will become apparent through reference to the following description and the accompanying drawings. Furthermore, it is to be understood that the features of the various embodiments described herein are not mutually exclusive and can exist in various combinations and permutations.

BRIEF DESCRIPTION OF THE DRAWINGS

In the following description, various embodiments are described with reference to the following drawings, in which.

DESCRIPTION

Embodiments generally relates to a multiple-sample-holder polishing setup for cross-section sample preparation. The setup could be retro-fitted onto existing standard polishing equipment. As such, the setup is inexpensive as no sophisticated gadgets or equipment are involved. Furthermore, reduction in cost of ownership may be attained from high throughput of samples. This multiple-sample-holder polishing setup can be used for cross-sectioning small, un-encapsulated samples such as integrated circuit (IC) chips and other electronic devices.

Figure 1:
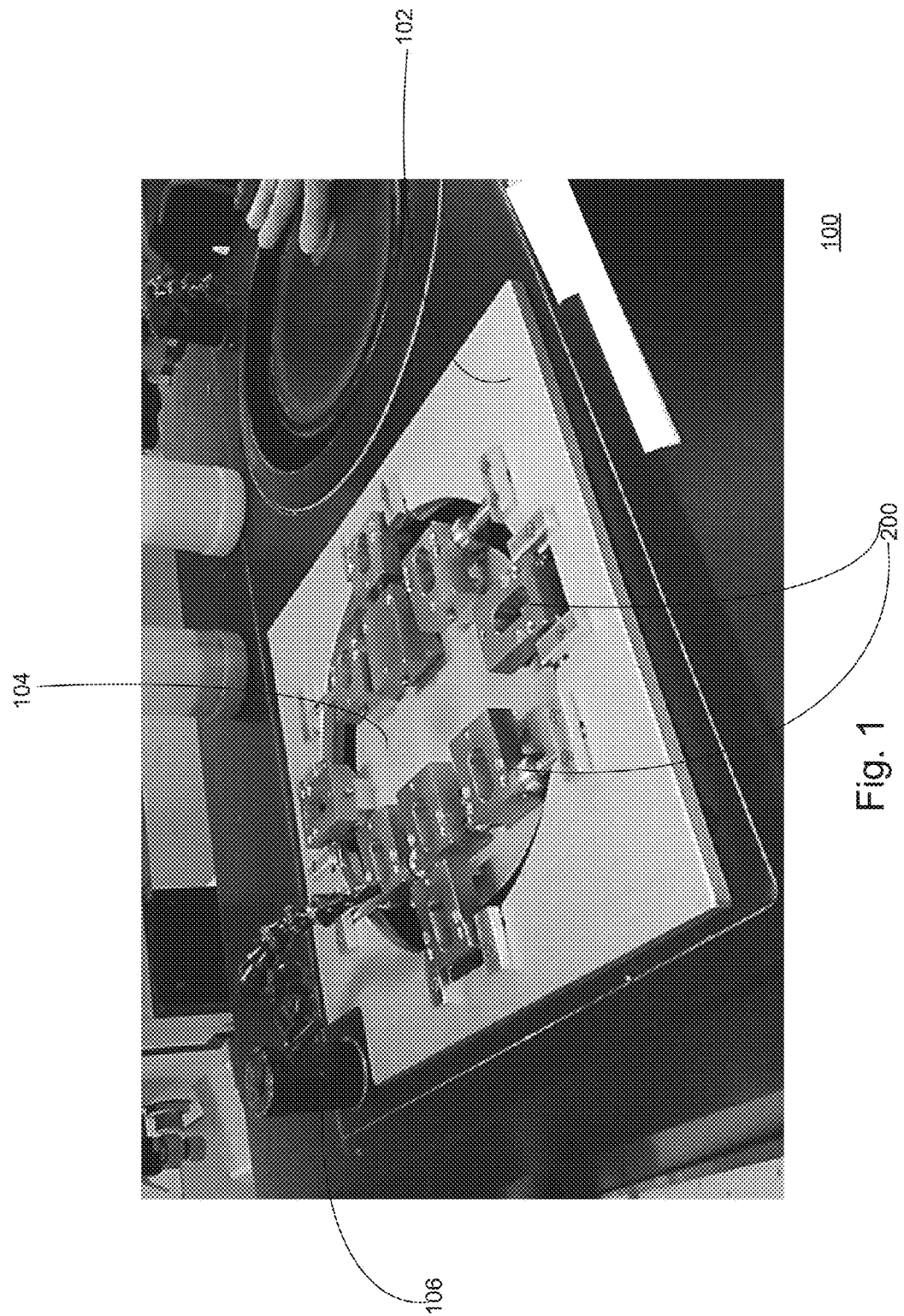
FIG. 1 shows an embodiment of a multiple-sample-holder polishing setup for cross-section sample preparation.

FIG. 1 shows an embodiment of a multiple-sample-holder polishing setup for cross-section sample preparation. As shown, the multiple-sample-holder polishing setup 100 includes a frame 102 and a platen with its surface covered with a polishing cloth 104 in the center of frame 102. The multiple-sample-holder polishing setup 100 also includes a polishing head or polisher 106, and a plurality of sample holders 200 that are placed on axial rods of the frame 102. For illustration purpose, the setup 100 includes about, for example, 10 sample holders. The setup may include other suitable numbers of sample holders. As can be seen, the multiple-sample holder polishing setup 100 allows for, for example, about ten (10) samples (not shown) to be polished concurrently without any intervention from the user. In addition, the multiple-sample-holder polishing setup 100 allows for the quick optical inspection of the specimen without the need to demount the sample from sample holder 200.

Figure 2F:
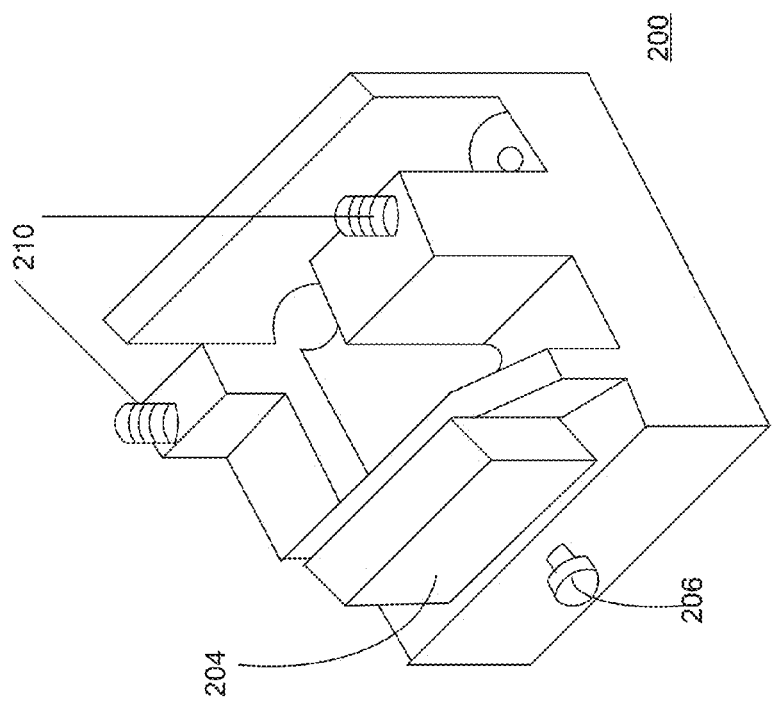
FIGS. 2(*a*)-2(*f*) show alternate views of an embodiment of a sample holder for use with the multiple-sample-holder polishing setup as shown in FIG. 1.

FIGS. 2(a)-2(f) show alternate views of an embodiment of a sample holder 200 for use with the multiple-sample-holder polishing setup 100. Referring to FIG. 2(a), a top view of sample holder 200 is presented. As can be seen, sample holder 200 includes a first pair of adjustment elements 202, such as screws, for coarse leveling adjustment of sample holder 200 by moving the screws further in or out. In other embodiments, other adjustment elements 210 for fine leveling adjustment of sample holder 200 may also be useful as the sample holders need to be adjustable to ensure that the cross-section area of interest could be evenly revealed on the sample. The adjustment is especially important when the site of interest is about to be reached as the site of interest may arrive at an undesirable tilt angle, in which case, the sample holders would need to be adjusted so the cross section could be evenly revealed to ensure accurate physical dimension measurement.

The first pair of adjustment elements 202 also ensures that the cutting direction is parallel when an integrated circuit (IC) device sample is fixed on a paddle 204 (not shown in FIG. 2(a)). First pair of adjustment elements 202 may be made from stainless steel. In other embodiments, the first pair of adjustment elements 202 may be made from other materials. Sample holder 200 also includes a fastener 206, such as screw, for securing the paddle 204 to sample holder 200. The sample holder, for example, may include a single fastener. The fastener 206, for example, may be made from stainless steel or from other materials in other embodiments.

FIG. 2(b) shows a side view of sample holder 200 where the paddle 204 may be clearly seen. FIG. 2(c) shows a bottom view of sample holder 200 where paddle 204 may be clearly seen and an IC device sample 208 attached to paddle 204 may be glimpsed. A second pair of adjustment elements 210, such as screws, which is in close proximity to the first pair of adjustment elements 202, can also be seen. Other suitable types of adjustment elements may also be used. FIG. 2(d) shows a bottom view of sample holder 200 when viewed from back. In this view, the second pair of adjustment elements 210 can be more clearly seen. The second pair of adjustment elements 210 is designed to stand on the polishing cloth of the rotating platen 104 and is used for fine leveling adjustment of sample holder 200. The second pair of adjustment elements 210 may be made of Teflon as Teflon is resistant to material removal while sitting on the polishing cloth of the rotating platen 104 but other materials that exhibit the same or similar characteristics may also be used.

Figure 2E:
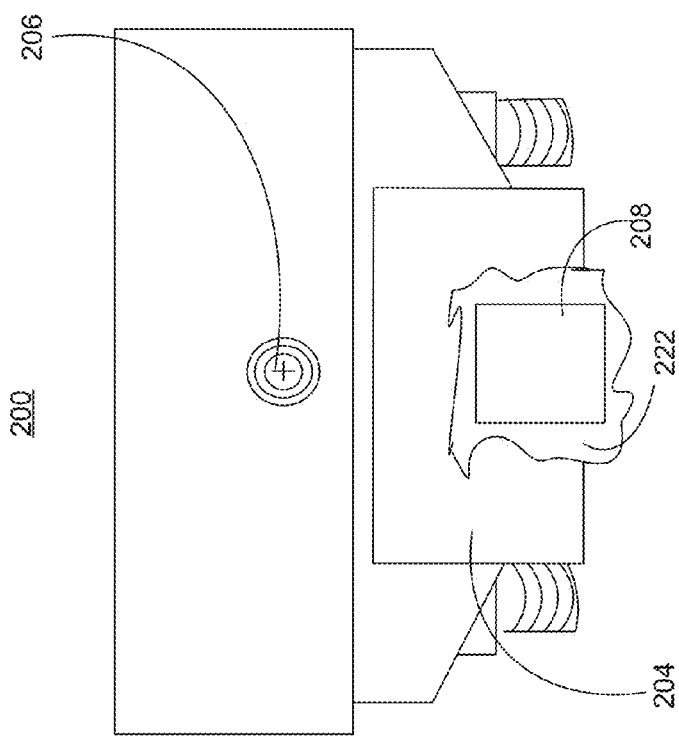

FIG. 2(e) shows a front view of sample holder 200, which shows clearly the IC device sample 208 being coated with an epoxy layer 222 and attached to paddle 204. IC device sample 208 may be attached to paddle 204 by, for example, wax. In other embodiments, other materials may be used for attaching IC device sample 208 to paddle 204. As can be seen, epoxy layer 222 includes a very thin layer thereby allowing for easy inspection for site of interests as well as quick material removal. In addition, the thin epoxy layer 222 will protect the cover of the IC device sample 208 to prevent damage during sample preparation. Epoxy layer 222, in one embodiment, may have a thickness of about 2 mm. In other embodiments, epoxy layer 222 may have a thickness of about 2 mm-3 mm. Other suitable thickness ranges may also be useful.

FIG. 2(f) shows a side view of sample holder 200 from an angle which shows more clearly the second pair of adjustment elements 210 and fastener 206 for securing paddle 204 to sample holder 200. Paddle 204 is inserted into sample holder 200 and its position made secure by fastener 206. Paddle 204, with sample 208 attached to it, may be taken out from sample holder 200 for inspection in a SEM or other similar microscopes. After the SEM inspection, paddle 204 could be easily repositioned back into sample holder 200 again for polishing throughout a polish-inspect-polish procedure. In other embodiments, the paddle may be examined by an optical microscope or other similar microscope, in which case, there would be no need to take out the paddle as inspection can be carried out directly under the optical microscope with the paddle attached to the holder.

Figure 3A:
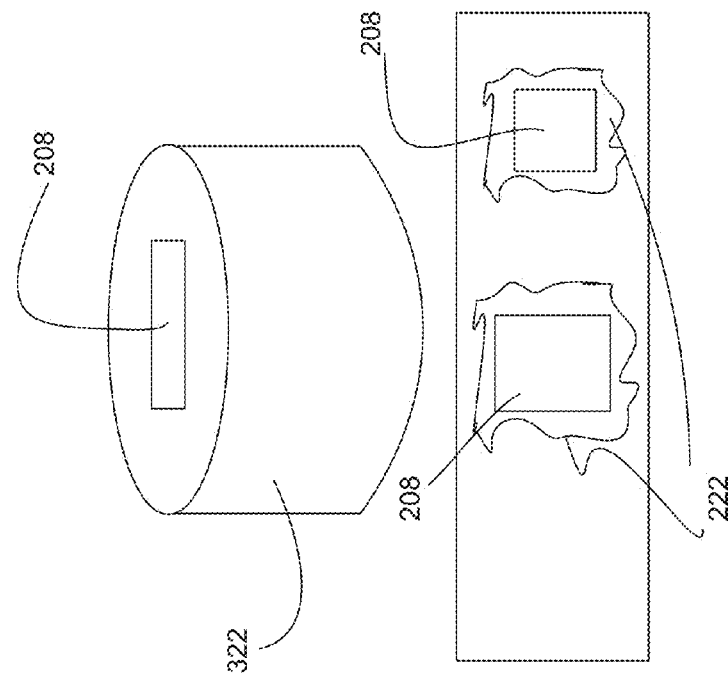
FIGS. 3(*a*)-3(*c*) show an embodiment of sample preparation, and different views of, respectively, a paddle and a sample holder.
Figure 3A:
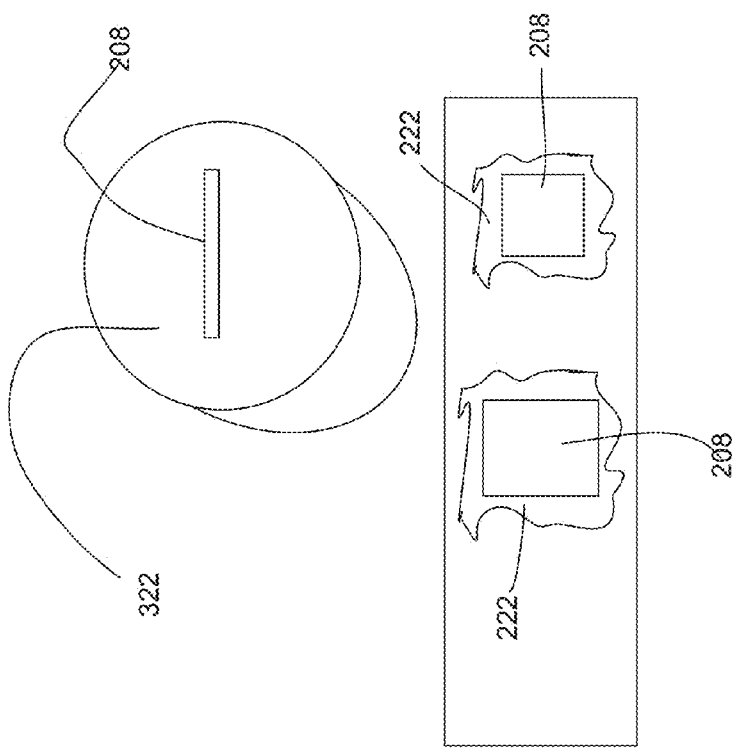

FIGS. 3(a)-3(c) show an embodiment of sample preparation, and of different views of a paddle and a sample holder, respectively. As can be seen, FIG. 3(a) shows an embodiment of sample protection by thin epoxy coating 222 as compared with a conventional method of enclosing the sample 208 within a thick cylindrical epoxy 322. As previously discussed, having a thin epoxy coating makes it very easy to inspect the sample 208; furthermore, this eliminates the need to shape the epoxy into a cylindrical shape, which has the aforementioned problem as stated in the Background.

FIG. 3(b) shows respectively from left to right and top to bottom, the front, right side and top view of paddle 204. As can be seen, paddle 204 has a main body 304 with an extension 306 extending out from main body 304. Extension 306 is the part of paddle 204 that is inserted into sample holder 200 and secured by fastener 206. Paddle 204 may be made of aluminum, which unlike steel, does not interfere with the electron beam of SEM and hence would not result in beam distortion during imaging. In other embodiments, materials with the same or similar characteristics as Aluminum may also be used. As previously mentioned, in some embodiments, paddle 204, with sample 208 attached to it, may be placed directly into most SEMs for direct viewing of cross-section without the need to demount sample 208.

In one embodiment, paddle 204 may have a width of about 1.9 cm with a height of about 1 cm, and a depth of about 0.5 cm. Hence, the sample 208 may only have a maximum surface area dimension of 1.9 cm×cm; however, in another embodiment, sample 208 may also have a larger dimension as it may be placed slightly protruding from the paddle. Alternatively, in yet other embodiments, other dimensions for paddle 204 may also be useful.

FIG. 3(c) shows, respectively from left to right and top to bottom, the top, right side and front view of sample holder 200. The width of the sample holder 200 may be about 3.6 cm or approximately 2 times the width of paddle 204. Other dimensions may also be helpful as long as it can ensure that uniform force is exerted on paddle 204 while the sample 208 is being polished. Sample holder 200 has been designed to prevent rocking during polishing and as such, is stable, well-balanced and has a low center of gravity.

As shown in the top view of sample holder 200 in FIG. 3(c), sample holder 200 has a hollow center 310 to reduce the overall weight of sample holder 200. This is to prevent over-exertion of force (from the weight of the sample holder 200) onto paddle 204 while the sample 208 is being polished. Weight balance is important to ensure an even polishing surface. Excessive sample holder weight will result in scratch marks as the platen with polishing cloth 104 is rotating, causing damage to the polishing cloth and the sample. In addition, the height of sample holder 200 is designed in such a way that it could be placed directly under the objective lens of most optical microscopes for immediate specimen inspection, without the need to demount paddle 204 from sample holder 200.

FIG. 3(c) also shows the first pair of adjustment elements 202, second pair of adjustment elements 210 and fastener 206. As shown, an extended part 312 of sample holder 200 is where the second pair of adjustment elements 210 may be located on sample holder 200. Paddle 204, on which sample 208 is attached, may be positioned flushed against an extended part 314 on sample holder 200. Sample holder 200 may be made from Copper, or in other embodiments, be made from other rust-proof or corrosive-resistant materials as the equipment would be used in a humid laboratory environment.

Figure 4A:
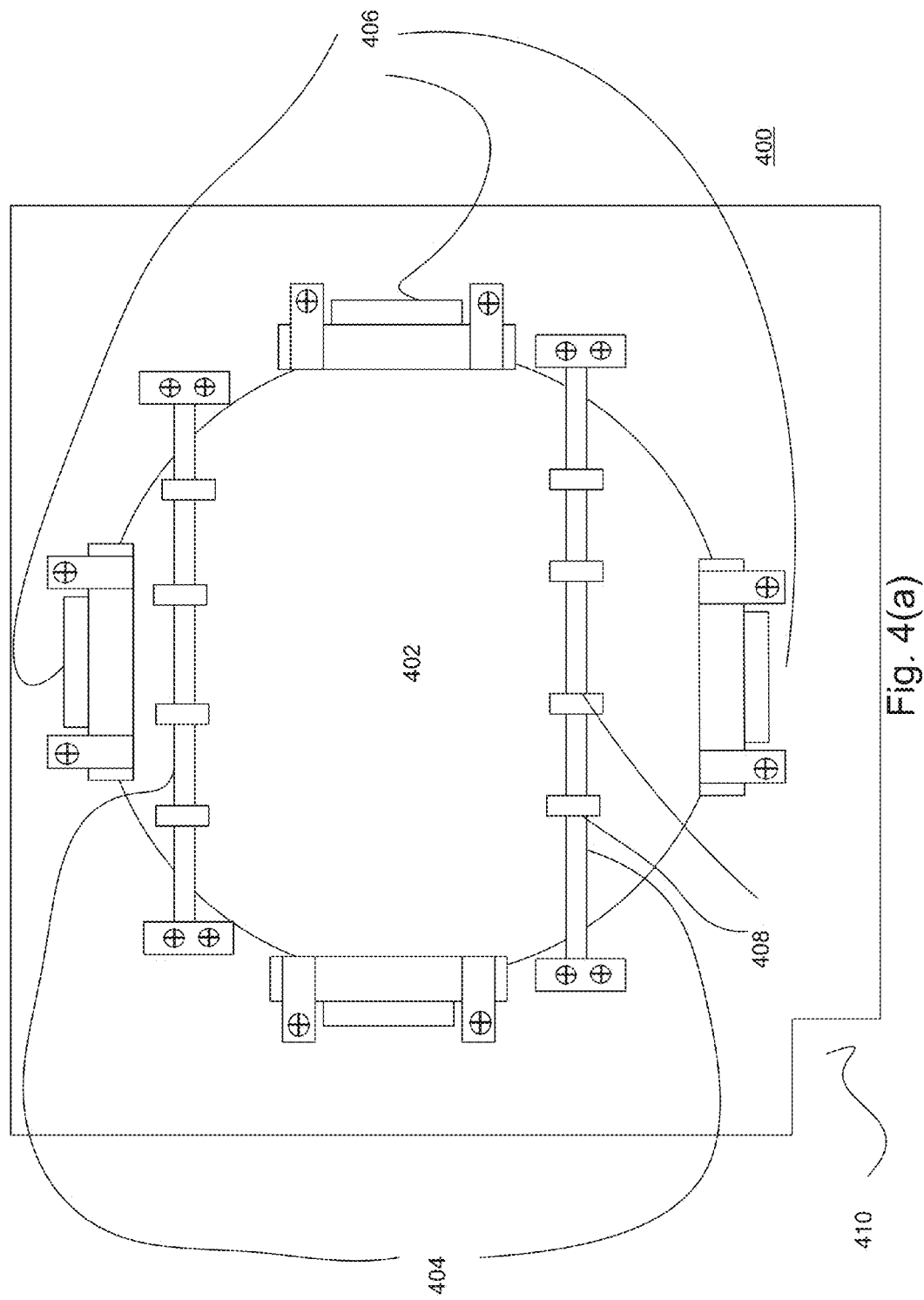
FIGS. 4(*a*) and 4(*b*), respectively, show an embodiment of a frame of the multiple-sample-holder polishing setup as shown in FIG. 1, without and with sample holders attached.

FIGS. 4(a) and 4(b), respectively, show an embodiment of a frame of the multiple-sample-holder polishing setup as shown in FIG. 1, without and with sample holders attached. As can be seen, FIG. 4(a) shows a frame 400 with no sample holders attached. Referring to FIG. 4(a), frame 400 has a hollow circular center 402 to allow polishing platen with polishing cloth 104 to fit within frame 400. Frame 400 also has 2 long rods 404 across frame 400 and 4 short rods 406 at the circumference of frame 400. The long rods 404 may be about 24 cm, and the short rods 406 may be about 7 cm but other dimensions may also be useful. Other suitable dimensions may also be useful. The long rods 404 may have rings 408 attached thereto. Sample holder 200 may be placed on the short rods 406 or affixed by fasteners (not shown), such as screws, on rings 408 on long rods 404. Frame 400 may further have a recessed corner 410 for accommodating a polishing tap (not shown).

FIG. 4(b) shows frame 400 with sample holders 200 attached thereto. As can be seen, each short rod 406 can accommodate, for example, about one sample holder 200. Meanwhile, each long rod 404 can accommodate, for example, about 3 sample holders 200. Other configurations may also be useful. As such, FIG. 4(b) shows that a total of, for example, 10 sample holders 200 may be placed on frame 400. However, in other embodiments, frame 400 may be able to hold other numbers of sample holders. Rings 408 on long rods 404, besides affixing the sample holders 200 to long rods 404, may also be used to shift the sample holders 200 to different locations on rods 404. Since a total of, for example, 10 sample holders can be placed on frame 400, this means that 10 samples 208, for example, may be polished concurrently, thereby potentially increasing sample preparation throughput by 10 times.

In addition, the frame 400 is designed to achieve, for example, four different polishing conditions, namely high grinding rate, edge-rounding, moderate grinding rate and low stress slow grinding rate. The positioning of the sample holders on frame 400 is important to achieve the desired polishing results as the rotation direction of the platen with polishing cloth 104 will have different effects on the sample holders 200 on different locations on frame 400. For example, when the polishing platen 104 is rotating in an anti-clockwise direction, the samples 208 placed in sample holders 200 in the respective holding positions (HP) will experience the following grinding conditions: (1) high stress fast grind rate (for HP4 and HP7), (2) edge rounding (for HP2 and HP9), (3) moderate stress with medium grind rate (for HP3 and HP8) and (4) low stress slow grind rate (for HP1, HP5, HP6, HP10).

The samples 208 could first be placed at sample holders 200 in the high stress fast grind rate positions (HP4 and HP7) for fast material removal and rapid approach to the region of interest. However, the cross-section surface is expected to be rough as the grinding rate is high. The sample holders 200 could then be placed at the edge rounding position (HP2 and HP9) to smoothen the rough cross-section surface. At this higher grinding rate, a nylon polishing cloth could be used together with colloidal diamond suspensions. The colloidal diamond grain size could be gradually reduced in the following order, for example, 30 µm, 15 µm, 5 µm, 1 µm and 0.25 µm, to achieve a smooth cross-section surface. Other suitable dimensions may also be useful.

After the cross-section surface has been considerably smoothened, the samples 208 could be placed in sample holders 200 at positions with medium grind rate (HP3 and HP8) for stable approach to the region of interest. When the region of interest is about to be reached, the grinding rate needs to be reduced and the sample holders 200 could be placed at positions HP1, HP5, HP6 and HP10. Slow grind rate is important to ensure cross-section surface uniformity. For final polishing, the colloidal diamond grain size could be changed from, for example, 0.25 µm to 0.10 µm. Other suitable dimensions may also be useful. The sample holders 200 could be physically swapped between the respective positions for the desired polishing outcomes. Alternatively, the rotation of the platen with polishing cloth could be turned from anti-clockwise direction to clockwise direction to achieve the toggling effects.

Figure 5:
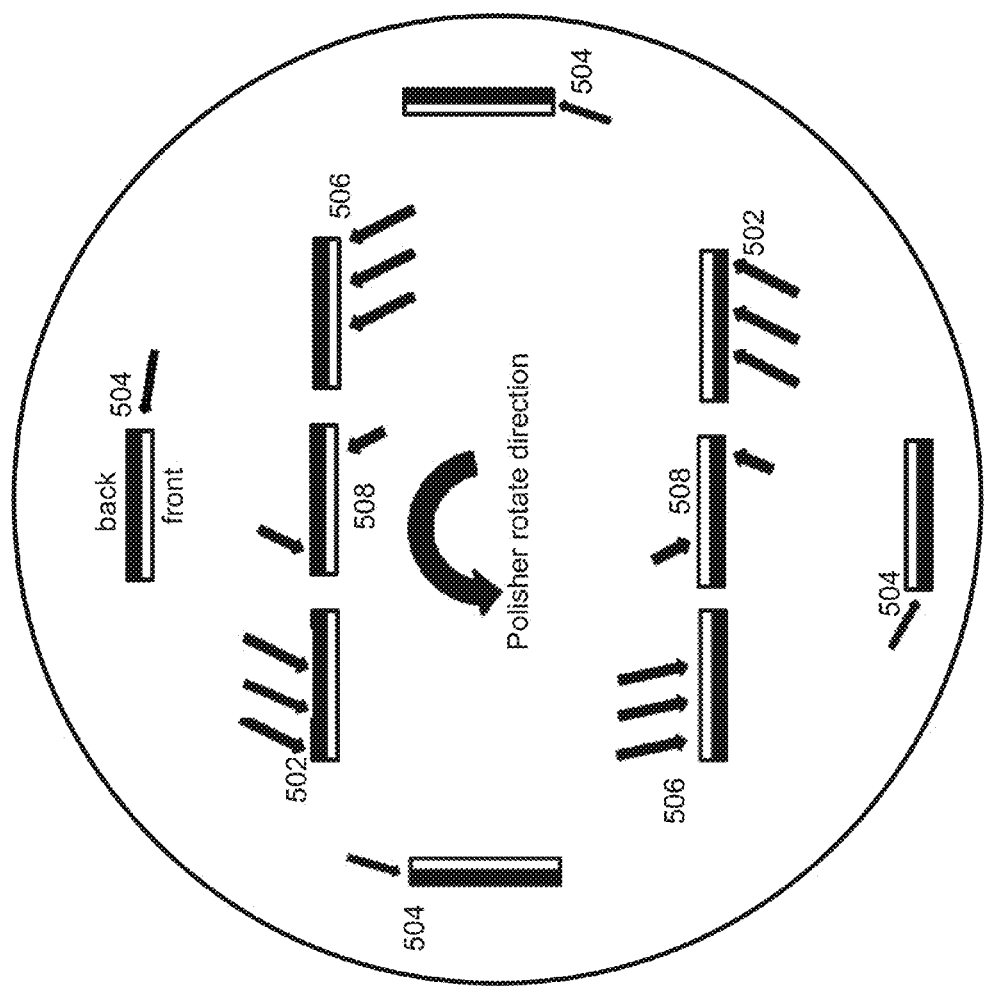
FIG. 5 shows the effects of sample position on the polishing effects.

FIG. 5 shows the effects of the sample position on the polishing effects. For example, sample 208 in sample holder 200 at position 502 is in a colloidal silica position and will experience edge rounding polishing. This position is good for, for example, faster grinding for the backside of the sample. On the other hand, sample 208 in sample holder 200 seated at the edge of the polisher (at position 504) is in a low stress position and will experience a low grinding rate. Sample 208 in sample holder 200 at position 506 is also in a high stress position and will experience a high grinding rate, which is good for fast grinding of the IC side of the sample. Finally, sample 208 in sample holder 200 at position 508 is in a medium stress position and will experience a medium grinding rate.

In yet other embodiments, the multiple-sample-holder polishing setup may be used in a method for making a device. The method includes providing one or more samples; providing a multiple-sample-holder polishing setup including a frame having more than one sample holders affixed thereto; affixing a paddle to each of the sample holders, the paddle having the sample attached thereto; and polishing the sample, wherein the sample is coated with a thin epoxy layer prior to polishing thereby allowing for easy inspection for site of interests as well as quick material removal. The thin epoxy layer also protects the sample from damage during sample preparation.

The above setup is mainly designed for preparation of samples for characterization or failure analysis. After cross-sectional polishing and inspection of the samples, information such as failing mechanisms or actual dimension of the structures on the sample could be obtained. Some examples of the failing mechanisms could be, but are not limited to, incomplete etching of the comb structures in a MEMS device, broken or shorted wiring routes, voids in electrical connections or physical structures which did not meet the target manufacturing dimension.

As such, after the inspection process is completed, the data are then collated and analyzed. This data or information is then feedback to the process integration department where the device fabrication parameters are then tuned and adjusted accordingly to better meet the design target for the next batch of wafers. The correspondence between the failure analysis and process integration team is an iterative improvement process until the desired yield has been achieved. After tuning the process parameters, front end of line processes and/or back end of line processes may be performed to complete the fabrication of the next batch of wafers. These processes may include common process steps to finish manufacturing of the semiconductor device, such as but are not limited to forming contacts to transistors, forming one or more interconnect levels, final passivation, dicing, assembly, packaging, etc. Other processes are also useful.

The invention may be embodied in other specific forms without departing from the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. A multiple-sample-holder polishing setup for cross-section sample preparation comprising:
    a frame, the frame having a hollow center, one or more long rods, one or more short rods and a recess, wherein the one or more long rods and the one or more short rods are configured to accommodate one or more sample holders and the recess is configured for accommodating a polishing head;
    one or more sample holders, the one or more sample holders to be directly attached to the one or more long rods and the one or more short rods of the frame;
    a paddle affixed to each sample holder; and
    a sample attached to the paddle, wherein the sample is coated with a thin epoxy layer prior to polishing thereby allowing for easy inspection for site of interests as well as quick material removal, and wherein the one or more long rods and the one or more short rods are configured to allow the one or more sample holders to be placed on different positions on the frame so that the sample in the sample holders will experience different polishing conditions on the same frame.

2. The polishing setup of claim 1 wherein the sample attached to the paddle may be taken out from the sample holder for inspection in a SEM or other similar microscopes.

3. The polishing setup of claim 1 wherein the sample attached to the paddle may be inspected without the need to take the paddle out from the sample holder as inspection can be carried out directly under an optical or similar microscope with the paddle attached to the sample holder.

4. The polishing setup of claim 1 wherein the one or more long rods are disposed across the frame and the one or more short rods are disposed at circumference of the frame.

5. The polishing setup of claim 1 wherein the different polishing conditions comprise high grinding rate, edge-rounding, moderate grinding rate and slow grinding rate.

6. The polishing setup of claim 5 comprising a polishing platen, wherein positioning of the sample holders on the frame will result in the sample experiencing different polishing conditions against the polishing platen and the sample may be polished under different polishing conditions by changing the position of the sample holder on the frame.

7. The polishing setup of claim 6 wherein the sample may be placed at a position on the frame with high grinding rate for fast material removal and rapid approach to a region of interest, followed by placement at an edge rounding position on the frame to smoothen a rough cross-section surface.

8. The polishing setup of claim 7 wherein the sample may further be placed at a position on the frame with medium grind rate for stable approach to the region of interest, wherein upon imminent contact with the interest region, the sample may then be changed to a slow grinding rate position to ensure cross-section surface uniformity.

9. A method for preparing cross-section samples comprising:
    providing a frame having a hollow center and one or more long rods and one or more short rods with one or more sample holders affixed thereto;
    affixing a paddle to each of the one or more sample holders, the paddle having a sample attached thereto;
    placing the one or more sample holders on different positions on the frame so that the sample in the sample holders will experience different polishing conditions; and
    polishing the sample, wherein the sample is coated with a thin epoxy layer prior to polishing thereby allowing for easy inspection for site of interests as well as quick material removal.

10. The method of claim 9 further comprising inspection of the sample attached to the paddle by removal of the paddle from the sample holder for inspection in a SEM or other similar microscopes.

11. The method of claim 9 further comprising inspection of the sample attached to the paddle by direct inspection of the sample under an optical or similar microscope with the paddle attached to the sample holder.

12. The method of claim 9 wherein the different polishing conditions comprise high grinding rate, edge-rounding, moderate grinding rate and slow grinding rate.

13. The method of claim 12 wherein positioning of the sample holders on the frame is changed as the frame rotates in an anti-clockwise direction against a polishing platen.

14. The method of claim 13 wherein the rotation of the polishing platen could be turned from anti-clockwise direction to clockwise direction to achieve a toggling effect.

15. The method of claim 9 further comprising physically swapping the sample holders between respective positions on the frame for achieving different polishing outcomes for the sample in the sample holders.

16. The method of claim 14 further comprising:
    placing the sample holder at a position on the frame with high grinding rate for fast material removal and rapid approach to a region of interest on the sample;
    placing the sample holder at an edge rounding position on the frame to smoothen a rough cross-section surface on the sample;
    placing the sample at a position on the frame with medium grind rate for stable approach to the region of interest on the sample; and
    placing the sample holder at a slow grinding rate position to ensure cross-section surface uniformity upon imminent contact with the interest region.

17. The polishing setup of claim 1 wherein the sample holder comprises a first pair of adjustment elements for coarse leveling adjustment and a second pair of adjustment elements for fine leveling adjustment.

18. The polishing setup of claim 1 wherein the sample holder comprises a hollow center to reduce overall weight of the sample holder to prevent over exertion of force onto the paddle while the sample is being polished.

19. The polishing setup of claim 1 wherein the thin epoxy layer coated on the sample protects the sample to prevent damage during sample preparation and comprises a thickness of about 2-3 mm.

20. The method of claim 9 wherein the one or more sample holders comprise:
- a first pair of adjustment elements configured for coarse leveling adjustment of the sample holder to ensure that cross-section area of interest on the sample could be evenly revealed on the sample; and
- a second pair of adjustment elements configured to stand on a polishing cloth of a rotating platen and configured for fine leveling adjustment of the sample holder.

\* \* \* \* \*